United States Patent
Brammer

(10) Patent No.: US 8,513,469 B2
(45) Date of Patent: Aug. 20, 2013

(54) HYDROFORMYLATION PROCESS WITH DOUBLY OPEN-ENDED BISPHOSPHITE LIGAND

(75) Inventor: Michael A. Brammer, Hurricane, WV (US)

(73) Assignee: Dow Technology Investments LLC

( * ) Notice: Subject to any disclaimer, the term of this patent is extended or adjusted under 35 U.S.C. 154(b) by 67 days.

(21) Appl. No.: 13/260,572

(22) PCT Filed: Dec. 10, 2009

(86) PCT No.: PCT/US2009/067416
§ 371 (c)(1),
(2), (4) Date: Sep. 27, 2011

(87) PCT Pub. No.: WO2010/117391
PCT Pub. Date: Oct. 14, 2010

(65) Prior Publication Data
US 2012/0029242 A1    Feb. 2, 2012

Related U.S. Application Data

(60) Provisional application No. 61/165,039, filed on Mar. 31, 2009.

(51) Int. Cl.
*C07C 45/50* (2006.01)
(52) U.S. Cl.
USPC .......................................................... 568/454
(58) Field of Classification Search
USPC .......................................................... 568/454
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,215,077 A | 7/1980 | Matsumoto et al. |
| 4,491,675 A | 1/1985 | Abatjoglou et al. |
| 4,518,809 A | 5/1985 | Forster et al. |
| 4,528,403 A | 7/1985 | Tano et al. |
| 4,593,011 A | 6/1986 | Abatjoglou et al. |
| 4,668,651 A | 5/1987 | Billig et al. |
| 4,717,775 A | 1/1988 | Billig et al. |
| 4,769,498 A | 9/1988 | Billig et al. |
| 4,774,361 A | 9/1988 | Maher et al. |
| 4,885,401 A | 12/1989 | Billig et al. |
| 5,059,710 A | 10/1991 | Abatjoglou et al. |
| 5,102,505 A | 4/1992 | Sorensen |
| 5,110,990 A | 5/1992 | Blessing et al. |
| 5,114,473 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,264,616 A | 11/1993 | Roeper et al. |
| 5,288,918 A | 2/1994 | Maher et al. |
| 5,364,950 A | 11/1994 | Babin et al. |
| 5,449,653 A | 9/1995 | Briggs et al. |
| 5,731,472 A | 3/1998 | Leung et al. |
| 5,874,639 A | 2/1999 | Nicholson et al. |
| 5,874,640 A | 2/1999 | Bryant et al. |
| 5,874,641 A | 2/1999 | Burke et al. |
| 5,910,600 A * | 6/1999 | Urata et al. ................... 558/162 |
| 5,932,772 A | 8/1999 | Argyropoulos et al. |
| 5,952,530 A | 9/1999 | Argyropoulos et al. |
| 6,090,987 A | 7/2000 | Billig et al. |
| 6,153,800 A | 11/2000 | Gelling et al. |
| 6,294,700 B1 | 9/2001 | Kanel et al. |
| 6,303,829 B1 | 10/2001 | Kanel et al. |
| 6,303,830 B1 | 10/2001 | Argyropoulos et al. |
| 6,307,109 B1 | 10/2001 | Kanel et al. |
| 6,307,110 B1 | 10/2001 | Argyropoulos et al. |
| 6,831,035 B2 | 12/2004 | Puckette et al. |
| 6,906,225 B2 | 6/2005 | Puckette et al. |
| 2006/0224000 A1 | 10/2006 | Papp et al. |
| 2007/0123735 A1 | 5/2007 | Jeon et al. |
| 2008/0065091 A1 | 3/2008 | Scribner et al. |

FOREIGN PATENT DOCUMENTS

| | | |
|---|---|---|
| CN | 1986055 | 6/2007 |
| JP | 2006143653 | 6/2006 |
| KR | 1020060118369 | 11/2006 |
| WO | 2011102990 | 8/2001 |

* cited by examiner

Primary Examiner — Sikarl Witherspoon
(74) Attorney, Agent, or Firm — Paul D. Hayhurst

(57) ABSTRACT

A continuous hydroformylation process for producing at least one aldehyde product by utilizing a transition metal and a ligand mixture comprising an organopolyphosphite and an organomonophosphine, with improved stability of the organopolyphosphite ligand. The process involves reacting one or more olefinically-unsaturated compounds with carbon monoxide and hydrogen in the presence of an organopolyphosphite ligand and an organomonophosphine ligand, at least one of such ligands being bonded to a transition metal to form a transition metal-ligand complex hydroformylation catalyst. Surprisingly the addition of the organomonophosphine to a Rh/organopolyphosphite catalyst system did not result in a significant loss of reaction rate.

11 Claims, No Drawings

HYDROFORMYLATION PROCESS WITH DOUBLY OPEN-ENDED BISPHOSPHITE LIGAND

CROSS-REFERENCE TO RELATED APPLICATIONS

This application is a 371 of PCT/US2009/067416 filed Dec. 10, 2009,which claims the benefit of U.S. Provisional Application Ser. No. 61/165,039, filed Mar. 31, 2009.

BACKGROUND OF THE INVENTION

This disclosure pertains to an improved process for hydroformylating an olefinically-unsaturated compound to produce one or more aldehyde products.

It is well known in the art that one or more aldehyde products can be produced by contacting under reaction conditions an olefinically-unsaturated compound with carbon monoxide and hydrogen in the presence of a metal-organophosphorus ligand complex catalyst. One such process, as exemplified in U.S. Pat. Nos. 4,148,830, 717,775, and 4,769, 498, involves continuous hydroformylation with recycle of a solution containing the metal-organophosphorus ligand complex catalyst, more preferably, a Group VIII-organophosphorus ligand complex catalyst. Rhodium is a preferred Group VIII metal. Organophosphines and organopolyphosphites are preferred organophosphorus ligands. Aldehydes produced by hydroformylation processes have a wide range of utility, for example, as intermediates for hydrogenation to aliphatic alcohols, for amination to aliphatic amines, for oxidation to aliphatic acids, and for aldol condensation to produce plasticizers.

While the benefits attendant with rhodium-organopolyphosphite ligand complexes for hydroformylation processes are well known, the stability of the organophosphite ligand remains a primary concern. Degradation of the organophosphite ligand can lead to catalyst poisons, inhibitors, or acidic byproducts that can lower catalyst activity or increase the rate of ligand loss. Because rhodium is extremely expensive, significant loss of catalytic activity can have a dramatic impact on process economics. Moreover, organopolyphosphite ligands are manufactured through multi-step syntheses, and are often quite expensive in their own right. In order for a rhodium-organopolyphosphite-based industrial hydroformylation process to be economically feasible, the ligand must be stabilized against the rigors of process conditions.

Numerous methods have been proposed to maintain catalyst and/or organophosphite stability through the addition of a second phosphorous-based compound. For instance, U.S. Pat. No. 6,153,800 describes adding sterically-hindered phosphines (e.g. tri(ortho-tolyl)phosphine) to stabilize a phosphite ligand against oxidative degradation. While less costly than the organophosphite ligand, the addition of tri(ortho-tolyl)phosphine) would significantly impact industrial process economics. Although less expensive, less sterically-hindered phosphines (e.g. triphenylphosphine; hereafter TPP) are effective in protecting the organophosphite, U.S. Pat. No. 6,153,800 teaches that they also significantly decrease the hydroformylation rate of the catalyst.

Organophosphite ligand stabilization is discussed in CN 1986055 A, which features the addition of tri(aryl)phosphines (e.g. TPP) to a rhodium/bisphosphite system. Although the bisphosphite ligand/TPP combination is more stabile than the bisphosphite alone, the hydroformylation reaction rate is significantly reduced. The loss in reaction rate can be recaptured by increasing the reaction temperature, but higher temperatures are known to increase the formation of aldehyde oligomer "heavies," which lowers the overall reaction efficiency.

Accordingly, it would be desirable to have a hydroformylation process employ a relatively inexpensive method for the stabilization of a rhodium/organophosphite ligand system that would not significantly reduce the inherent hydroformylation reaction rate of the system.

SUMMARY OF THE INVENTION

In one embodiment, the disclosure pertains to a hydroformylation process for continuous production of at least one aldehyde product, the process comprising the steps of: contacting under continuous reaction conditions in a hydroformylation reaction fluid, one or more olefinically-unsaturated compounds, carbon monoxide, and hydrogen in the presence of a mixture of a doubly open-ended organopolyphosphite ligand and an organomonophosphine ligand, at least one of said ligands being bonded to a transition metal to form a transition metal-ligand complex hydroformylation catalyst; the organopolyphosphite ligand comprising a plurality of phosphorus (III) atoms each bonded to three hydrocarbyloxy radicals, any non-bridging species of which consists essentially of an aryloxy radical (substituted or unsubstituted); the contacting being conducted in a manner such that the molar ratio of both the organomonophosphine and the organopolyphosphite to the metal is at least 1, i.e. the ratio of organomonophosphine to the metal is at least 1 and the ratio of organopolyphosphite to the metal is at least 1.

Surprisingly, the addition of the phosphine compound to the Rh/organopolyphosphite catalyst improves the stability of the organopolyphosphite ligand, but does not significantly adversely impact the selectivity (N:I ratio) or reaction rate of the system.

DETAILED DESCRIPTION OF THE INVENTION

The hydroformylation process of this disclosure for producing one or more aldehydes employs one or more olefinically-unsaturated compounds, carbon monoxide, hydrogen, and a mixture of a doubly open-ended organopolyphosphite ligand and an organomonophosphine ligand, at least one of said ligands being bonded to a transition metal to form a transition metal-ligand complex hydroformylation catalyst.

As described in detail hereinafter, the process of this disclosure comprises contacting under continuous reaction conditions in a hydroformylation reaction fluid, one or more olefinically-unsaturated compounds, carbon monoxide, and hydrogen in the presence of a mixture of an organopolyphosphite ligand and an organomonophosphine ligand, at least one of said ligands being bonded to a transition metal to form a transition metal-ligand complex hydroformylation catalyst. The organopolyphosphite ligand comprises a plurality of phosphorus (III) atoms each bonded to three hydrocarbyloxy radicals, any non-bridging species of which consists essentially of a substituted or unsubstituted aryloxy radical. The contacting is further conducted such that the molar ratio of both the organopolyphosphite ligand and the organomonophosphine ligand to transition metal is at least 1.

The hydroformylation process of this disclosure may be asymmetric or non-asymmetric, the preferred process being non-asymmetric, and is conducted in any continuous or semi-continuous fashion, and may involve any conventional catalyst-containing hydroformylation reaction fluid and/or gas and/or extraction recycle operation, as desired. As used herein, the term "hydroformylation" is contemplated to include all operable asymmetric and non-asymmetric processes that involve converting one or more substituted or unsubstituted olefinic compounds or a reaction mixture comprising one or more substituted or unsubstituted olefinic compounds, in the presence of carbon monoxide, hydrogen, and a hydroformylation catalyst, to a product comprising at least one substituted or unsubstituted aldehyde.

The substituted or unsubstituted olefinic compound employable in the hydroformylation process of this disclosure can include both optically active (prochiral and chiral) and non-optically active (achiral) unsaturated compounds containing from 2 to 40, preferably 3 to 20, carbon atoms and one or more carbon-carbon double bonds (C═C). Such olefinic compound can be terminally or internally unsaturated and be of straight-chain, branched chain, or cyclic structures. Olefin mixtures, such as obtained from the oligomerization of propene, butene, and isobutene, (such as, so called dimeric, trimeric or tetrameric propylene, as disclosed, for example, in U.S. Pat. Nos. 4,518,809 and 4,528,403, incorporated herein by reference) may also be employed, as well as mixed butenes, for example, raffinate I and raffinate II known to the skilled person. Such olefinic compounds and the corresponding aldehyde products derived therefrom may also contain one or more groups or substituents that do not adversely affect the hydroformylation process of this disclosure; suitable groups or substituents being described, for example, in U.S. Pat. Nos. 3,527,809, and 4,769,498, incorporated herein by reference.

Most preferably the process of the subject disclosure is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexene, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, for example, methyl pentenoate; alkenyl alkanoates, alkenyl alkyl ethers, alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, oleic acid and esters thereof, such as methyl oleate, and homologous unsaturated fatty acids and unsaturated fatty acid esters. Illustrative of suitable substituted and unsubstituted olefinic starting materials include those olefinic compounds described in Kirk-Othmer, *Encyclopedia of Chemical Technology, Fourth Edition,* 1996, the pertinent portions of which are incorporated herein by reference.

Hydrogen and carbon monoxide are also required for the process of this disclosure. These gases may be obtained from any available source, including petroleum cracking and refinery operations. Synthesis gas mixtures are preferably employed. The $H_2$:CO molar ratio of gaseous hydrogen to carbon monoxide may range, preferably, from about 1:10 to about 100:1, the more preferred $H_2$:CO molar ratio being from about 1:10 to about 10:1.

In the process of this disclosure, two different organophosphorus ligands are required, both of which are capable of bonding to a transition metal to form a transition metal-organophosphorus ligand complex catalyst capable of catalyzing the hydroformylation process. One organophosphorus ligand is required to comprise an organopolyphosphite ligand, while the other organophosphorus ligand is required to comprise an organomonophosphine ligand. As the organopolyphosphite ligand, one such ligand or a mixture of such ligands may be used. As the organomonophosphine ligand, one such ligand or a mixture of such ligands may be used.

The hydroformylation processing techniques applicable to this disclosure may correspond to any of the processing techniques known and described in the art. Preferred processes are those involving catalyst liquid recycle hydroformylation processes, as described in U.S. Pat. Nos. 4,668,651; 4,774,361; 5,102,505; 5,110,990; 5,288,918; 5,874,639; and 6,090,987; and extractive hydroformylation processes, as described in U.S. Pat. Nos. 5,932,772; 5,952,530; 6,294,700; 6,303,829; 6,303,830; 6,307,109; and 6,307,110; the disclosures of which are incorporated herein by reference.

Generally, such catalyzed liquid hydroformylation processes involve production of aldehydes by contacting an olefinic unsaturated compound with carbon monoxide and hydrogen in the presence of a transition metal-organophosphorus ligand complex catalyst in a liquid phase that may also contain an organic solvent for the catalyst and ligand. Free organophosphorus ligand is also present in the liquid phase. In this disclosure, the generic term "organophosphorus ligand" embraces both types of ligands: organopolyphosphite and organomonophosphine. Both ligands are required; but no inference is made that both ligands are always complexed to the transition metal. Rather, the ligands may be complexed or unbound as catalytic cycling and competition between ligands for transition metal may dictate. By "free organophosphorus ligand" is meant an organophosphorus ligand that is not complexed with (tied to or bound to) the metal, for example, rhodium atom, of the complex catalyst. Generally, the hydroformylation process may include a recycle method, wherein a portion of the liquid reaction fluid containing the catalyst and aldehyde product is withdrawn from the hydroformylation reactor (which may include one reaction zone or a plurality of reaction zones, for example, in series), either continuously or intermittently; and the aldehyde product is separated and recovered therefrom by techniques described in the art; and then a metal catalyst-containing residue from the separation is recycled to the reaction zone as disclosed, for example, in U.S. Pat. No. 5,288,918. If a plurality of reaction zones is employed in series, the reactant olefin may, in one embodiment of the disclosure, be fed to the first reaction zone only; while the catalyst solution, carbon monoxide, and hydrogen may be fed to each of the reaction zones, or, in another embodiment, the olefin may be fed into more than one of the reaction zones.

As used hereinafter, the term "reaction fluid" or "reaction product fluid" is contemplated to include, but is not limited to, a reaction mixture comprising: (a) an organopolyphosphite ligand, (b) an organomonophosphine ligand, (c) a transition metal-ligand complex catalyst wherein the ligand is selected from a mixture in the fluid of the organopolyphosphite ligand and the organomonophosphine ligand, (d) at least one aldehyde product formed in the reaction, (e) optionally, unconverted reactants including unreacted olefin, and (f) an organic solubilizing agent for said metal-ligand complex catalyst and said free ligand. It is to be understood that the hydroformylation reaction fluid may contain minor amounts of additional ingredients, such as those that have either been deliberately added or formed in situ during the process. Examples of such additional ingredients include carbon monoxide and hydrogen gases, and in situ formed products, such as saturated hydrocarbons, and/or unreacted isomerized olefins corresponding to the olefin starting materials, and/or high boiling liquid aldehyde condensation byproducts, and/or one or more degradation products of the catalyst and/or organophosphorus ligands, including by-products formed by hydrolysis of the organophosphorus ligands, as well as inert co-solvents or hydrocarbon additives, if employed.

Suitable metals that make up the transition metal-ligand complex catalyst include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other permissible metals include Group VIB metals selected from chromium (Cr), molybdenum (Mo), tungsten (W), and mixtures thereof. Mixtures of metals from Groups VIB and VIII may also be used.

The term "complex" as used herein means a coordination compound formed by the union of one or more electronically rich molecules or atoms (i.e., ligand) with one or more electronically poor molecules or atoms (i.e., transition metal). For example, the organomonophosphine ligand employable herein possesses one phosphorus (III) donor atom having one unshared pair of electrons, which is capable of forming a coordinate covalent bond with the metal. The organopolyphosphite ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefins, diolefins and triolefins, tetrahydrofuran, and the like.

The number of available coordination sites on the transition metal is well known in the art and depends upon the particular transition metal selected. The catalytic species may comprise a complex catalyst mixture in their monomeric, dimeric or higher nuclearity forms, which preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to either the organopolyphosphite ligand or the organomonophosphine ligand.

The organopolyphosphite ligand broadly comprises a plurality of phosphite groups, each of which contains one trivalent phosphorus atom bonded to three hydrocarbyloxy radicals. Hydrocarbyloxy radicals that link and bridge two phosphite groups are more properly referred to as "divalent hydrocarbyldioxy radicals." These bridging diradicals are not limited to any particular hydrocarbyl species.

The term "aryloxy" as used herein broadly refers to a monovalent substituted or unsubstituted aryl radical bonded to a single ether linkage, as in —O-aryl, wherein the aryl group comprises an aromatic ring or rings. Preferred aryloxy groups contain one aromatic ring, or from 2 to 4 fused or linked aromatic rings, each ring having from about 5 to about 20 carbon atoms such as, for example, phenoxy, naphthyloxy, or biphenoxy. Any of the aforementioned radicals and groups may be unsubstituted or substituted as noted hereinafter.

The term "end group" as used herein broadly refers to an aryloxy radical that is pendant from a phosphorus atom and not bridging two phosphite groups (i.e., terminal, non-bridging). In Formula I, below, the end groups are represented by $R_1$ and $R_2$, and are each required to consist essentially of an aryl radical.

The term "end group pair" as used herein broadly refers to two aryloxy radicals as defined above that are pendant from the same phosphorous atom. The term "open-ended" as used herein broadly refers to polyorganophosphite ligands wherein the aryloxy radicals comprising at least one of the end group pairs are not bonded to one another. The term "doubly open-ended" as used herein broadly refers to polyorganophosphite ligands wherein the aryloxy radicals comprising two of the end group pairs are not bonded to one another.

Preferred organopolyphosphite ligands comprise two, three, or higher numbers of phosphite groups. Mixtures of such ligands may be employed if desired. Achiral organopolyphosphites are preferred. Representative organopolyphosphites include those having the formula:

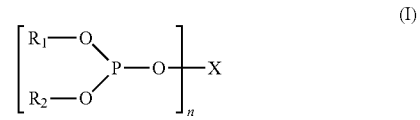

(I)

wherein n is from 2 to 4. X represents a substituted or unsubstituted n-valent organic bridging radical containing from 2 to 40 carbon atoms, $R_1$ and $R_2$ are the same or different and each represents an aryl radical end group containing from 6 to 40 carbon atoms, preferably from 6 to 24 carbon atoms, most preferably from 6 to 20 carbon atoms. These end group pairs are by definition open-ended. In a preferred embodiment, X is divalent.

Representative n-valent hydrocarbon bridging radicals represented by X include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, wherein each y is the same or different and has a value of 0 or 1, and wherein m has a value of 0 or 1. Q represents a divalent bridging group selected from —$C(R^3)_2$—, —O—, —S—, —$NR^4$—, —Si$(R^5)_2$— and —CO—, wherein each $R^3$ is the same or different and represents hydrogen, an alkyl radical having from 1 to 12 carbon atoms, phenyl, tolyl, or anisyl, $R^4$ represents hydrogen or a substituted or unsubstituted monovalent hydrocarbon radical, for example, an alkyl radical having 1 to 4 carbon atoms; and each $R^5$ is the same or different and represents hydrogen or an alkyl radical, preferably, a $C_{1-10}$ alkyl radical. The more preferred acyclic radicals represented by X above are divalent alkylene radicals, while the more preferred aromatic radicals represented by X above are divalent arylene and bisarylene radicals, such as disclosed more fully, for example, in U.S. Pat. Nos. 4,769,498; 4,774,361; 4,885,401; 5,179,055; 5,113,022; 5,202,297; 5,235,113; 5,264,616; 5,364,950; 5,874,640; 5,892,119; 6,090,987; and 6,294,700, the disclosures of which are incorporated herein by reference.

Moreover, if desired, any given organopolyphosphite in the above Formula (I) may be an ionic phosphite, that is, may contain one or more ionic moieties selected from the group consisting of: —$SO_3M$, wherein M represents an inorganic or organic cation, —$PO_3M$ wherein M represents an inorganic or organic cation, —$N(R^6)_3X^1$, wherein each $R^6$ is the same or different and represents a hydrocarbon radical containing from 1 to 30 carbon atoms, for example, alkyl, aryl, alkaryl, aralkyl, and cycloalkyl radicals, and $X^1$ represents an inorganic or organic anion, and —$CO_2M$ wherein M represents an inorganic or organic cation, as described, for example, in U.S. Pat. Nos. 5,059,710; 5,113,022; 5,114,473; and 5,449,653, the disclosures of which are incorporated herein by reference. Thus, if desired, such organopolyphosphite ligands may contain from 1 to 3 such ionic moieties; however, it is preferred that only one such ionic moiety be substituted on any given aryl moiety when the organopolyphosphite ligand contains more than one such ionic moiety. Suitable cationic species of M include, without limitation, hydrogen (that is, a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anions $X^1$ include, for example, sulfate, carbonate, phosphate, chloride, acetate, oxalate and the like.

Of course any of the $R^1$, $R^2$, X and Q radicals of such non-ionic and ionic organopolyphosphites of Formula (I) above may be substituted if desired, with any suitable substituent, optionally containing from 1 to 30 carbon atoms, that does not adversely affect the desired result of the process of this disclosure. Substituents that may be on said radicals in addition, of course, to corresponding hydrocarbon radicals such as alkyl, aryl, aralkyl, alkaryl and cyclohexyl substituents, may include for example silyl radicals such as —$Si(R^7)_3$; amino radicals such as —$N(R^7)_2$; phosphine radicals such as -aryl-$P(R^7)_2$; acyl radicals such as —$C(O)R^7$; acyloxy radicals such as —$OC(O)R^7$; amido radicals such as —$CON(R^7)_2$ and —$N(R^7)COR^7$; sulfonyl radicals such as —$SO_2R^7$, alkoxy radicals such as —$OR^7$; sulfinyl radicals such as —$SOR^7$; sulfenyl radicals such as —$SR^7$; phosphonyl radicals such as —$P(O)(R)_2$; as well as halogen, nitro, cyano, trifluoromethyl, hydroxy radicals, and the like, wherein preferably each $R^7$ radical individually represents the same or different monovalent hydrocarbon radical having from 1 to about 18 carbon atoms (for example, alkyl, cycloalkyl, aryl, aralkyl, alkaryl and cyclohexyl radicals), with the proviso that in amino substituents such as —$N(R^7)_2$ each $R^7$ taken together can also represent a divalent bridging group that forms a heterocyclic radical with the nitrogen atom, and in amido substituents such as —$C(O)N(R^7)_2$ and —$N(R^7)COR^7$ each $R^7$ bonded to N can also be hydrogen. Of course it is to be understood that any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl and naphthyl; aralkyl radicals such as benzyl, phenylethyl, and triphenylmethyl; alkaryl radicals such as tolyl and xylyl; alicyclic radicals such as cyclopentyl, cyclohexyl, 1-methylcyclohexyl, cyclooctyl, and cyclohexylethyl; alkoxy radicals such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals such as phenoxy; as well as silyl radicals such as —$Si(CH_3)_3$, —$Si(OCH_3)_3$, and —$Si(C_3H_7)_3$; amino radicals such as —$NH_2$, —$N(CH_3)_2$, —$NHCH_3$, and —$NH(C_2H_5)$; arylphosphine radicals such as —$P(C_6H_5)_2$; acyl radicals such as —$C(O)CH_3$, —$C(O)C_2H_5$, and —$C(O)C_6H_5$; carbonyloxy radicals such as —$C(O)OCH_3$; oxycarbonyl radicals such as —$O(CO)C_6H_5$; amido radicals such as —$CONH_2$, —$CON(CH_3)_2$, and —$NHC(O)CH_3$; sulfonyl radicals such as —$S(O)_2C_2H_5$; sulfinyl radicals such as —$S(O)CH_3$; sulfenyl radicals such as —$SCH_3$, —$SC_2H_5$, and —$SC_6H_5$; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, and —$P(O)(H)(C_6H_5)$.

Specific illustrative examples of such organobisphosphite ligands include the following:

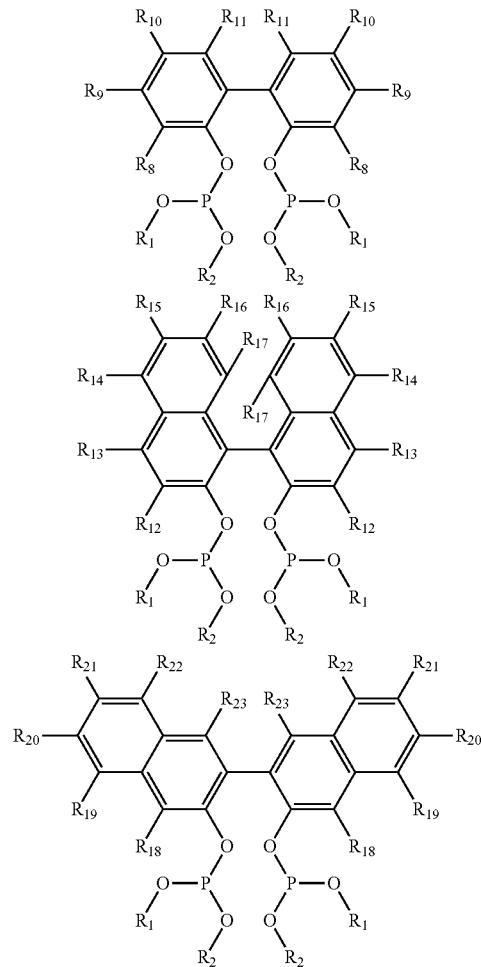

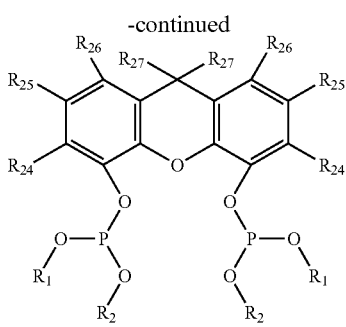

where $R_1$ and $R_2$ are as defined above, and $R_8$ through $R_{24}$ may be each independent of the other, a hydrogen atom, a $C_{1-20}$ alkyl, aryl, aralkyl, alkaryl or cyclohexyl substituents; alkoxy radicals such as methoxy, ethoxy, propoxy, t-butoxy, —OCH$_2$CH$_2$OCH$_3$, —O(CH$_2$CH$_2$)$_2$OCH$_3$, and —O(CH$_2$CH$_2$)$_3$OCH$_3$; aryloxy radicals such as phenoxy; silyl radicals such as —Si(R$^7$)$_3$; acyl radicals such as —C(O)R$^7$; acyloxy radicals such as —OC(O)R$^7$; amido radicals such as —CON(R$^7$)$_2$ and —N(R$^7$)COR$^7$ (where R$^7$ is as defined above); halogen, or trifluoromethyl.

In a more preferred embodiment, illustrative examples of such organobisphosphite ligands include the following:

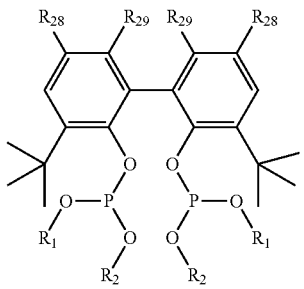

where $R_1$ and $R_2$ are as defined above, and $R_{28}$ may be a $C_{1-29}$ alkyl or cycloalkyl radical or an alkoxy radical; $R_{29}$ may be a hydrogen atom, a $C_{1-29}$ alkyl or cycloalkyl radical or an alkoxy radical.

In a most preferred embodiment, the organobisphosphite ligand is Ligand A:

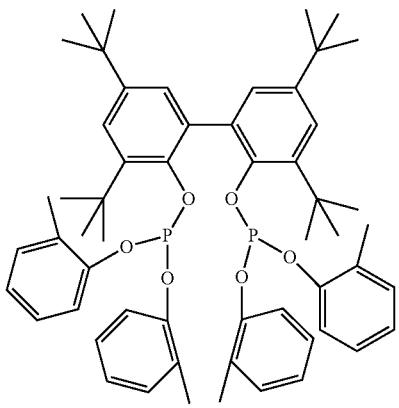 [SMILES: Cc1ccccc1OP(Oc1ccccc1C)Oc1c(-c2cc(C(C)(C)C)cc(C(C)(C)C)c2OP(Oc2ccccc2C)Oc2ccccc2C)cc(C(C)(C)C)cc1C(C)(C)C]

The organomonophosphine employable in the process of this disclosure comprises any organic compound comprising one phosphorus atom covalently bonded to three aryl or alkyl radicals, or combinations thereof. A mixture of organomonophosphine ligands may also be employed. Representative organomonophosphines include those having the formula:

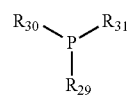

(II)

wherein each $R_{29}$, $R_{30}$ and $R_{31}$ may be the same or different and represent an alkyl radical, or a substituted or unsubstituted aryl radical containing from 4 to 40 carbon atoms or greater. Such organomonophosphines may be found described in greater detail, for example, in U.S. Pat. No. 3,527,809, the disclosure of which is incorporated herein by reference. Triphenyl phosphine, i.e. the compound of Formula II wherein each $R_{29}$, $R_{30}$ and $R_{31}$ is phenyl, is an example of a preferred organomonophosphine ligand.

The concentration of metal-ligand complex(es) present in the reaction fluid of the hydroformylation process of this disclosure need only be that minimum amount necessary to provide a metal concentration necessary to catalyze the desired hydroformylation process. Generally, in the hydroformylation of propylene, the metal concentration, preferably, rhodium concentration, is greater than about 1 part per million (ppm), and preferably, greater than about 20 ppm, based on the weight of the hydroformylation reaction fluid. Generally, in the hydroformylation of propylene, the metal concentration is less than about 500 parts per million (ppm), preferably, less than about 120 ppm, and more preferably less than about 95 ppm, based on the weight of the hydroformylation reaction fluid. For C4+ olefins, such as butene and those of higher molecular weights, suitable concentrations of metal may be higher, because higher olefins exhibit reduced activity as compared with propylene.

Both the organopolyphosphite and the organomonophosphine ligand employable in the process of this disclosure, including free and complexed forms, are provided to the process in a quantity such that the molar ratio of each ligand to the transition metal present in the hydroformylation reaction fluid is at least 1 (i.e., at least 1 mole of each ligand per mole transition metal). Preferably the quantity of each ligand is at least 2 moles per mole of transition metal.

The concentrations of transition metal, organopolyphosphite ligand, and organomonophosphine ligand in the hydroformylation reaction fluid can be readily determined by well known analytical methods. From these concentration analyses, the required molar ratios can be readily calculated and tracked. The transition metal, preferably rhodium, is best determined by atomic absorption or inductively coupled plasma (ICP) techniques. The ligands are best quantized by $^{31}$P nuclear magnetic resonance spectroscopy (NMR) or by high pressure liquid phase chromatography (HPLC) of aliquots of the reaction fluid. On-line HPLC can also be used to monitor the concentrations of the ligands and the transition metal-ligand complexes. The different ligands should be characterized separately (e.g., without the presence of transition metal in the reaction fluid) in a quantitative manner to establish chemical shifts and/or retention times using appropriate internal standards as needed. The transition metal-organopolyphosphite ligand and transition metal-organo-monophosphine ligand complexes can be observed via any of the above-identified analytical methods to enable quantification of the complexed ligand(s).

The concentration of either ligand in the hydroformylation reaction fluid can be increased or maintained in any suitable manner, for example, by adding a quantity of ligand all at one time or in incremental additions to the hydroformylation reactor. In one embodiment of the disclosure, the ligand concentration can be increased or maintained by continuously or intermittently adding a quantity of ligand in a solubilizing agent as a liquid feed to the reactor. Alternatively, additional ligand can be added into a recycle stream (or a unit that produces a recycle stream) at any point downstream of the hydroformylation reactor for cycling back to said reactor. At any time during the continuous hydroformylation process, additional organopolyphosphite and/or organomonophosphine ligand(s) can be supplied to the reaction fluid to make-up for such ligand lost through degradation.

In general, the hydroformylation process of this disclosure can be conducted at any operable reaction temperature. Preferably, the reaction temperature is greater than about −25° C., more preferably, greater than about 50° C. Preferably, the reaction temperature is less than about 200° C., preferably, less than about 120° C.

In general, the hydroformylation process of this disclosure can be conducted at any operable reaction pressure. Preferably, the reaction is conducted at a total pressure of at least about 15 psia (103.4 kPa), more preferably at least about 25 psia (172.4 kPa). Preferably, the reaction pressure is not more than about 2,000 psia (13,789.6 kPa), more preferably not more than about 300 psia (2,068.4 kPa).

The hydroformylation reactor is preferably equipped with an impeller, impeller shaft, olefin feed line and flow control, syngas feed line and flow control, a vent line and vent flow control, a total pressure sensor for sensing pressure within the reactor, an exit line for removing product fluid from the reactor, and an entry line for feeding recovered catalyst back to the reactor. The syngas feed line typically terminates in the reactor with a sparger. Optionally, the reactor may include one or more baffles that separate the inner chamber of the reactor into a plurality of reaction zones. Typically, each baffle is attached to the inner wall of the reactor and extends into the reactor perpendicular to the impeller shaft; and each baffle contains an opening or hole of sufficient size for passage of the impeller shaft as well as passage of reaction fluid and gases. Typically, each chamber or zone in the reactor formed by such baffles contains an impeller as well as a gas sparger for circulating and mixing the reaction fluid in that chamber or zone.

The syngas feed flow rate may be any operable flow rate sufficient to obtain the desired hydroformylation process. Typically, the syngas feed flow rate can vary widely depending upon the specific form of catalyst, olefin feed flow rate, and other operating conditions. Suitable syngas feed flow rates and vent flow rates are described in the following reference: "Process Economics Program Report 21D: Oxo Alcohols 21d," SRI Consulting, Menlo Park, Calif., Published December 1999, incorporated herein by reference.

Specific Embodiments of the Invention

The process of this disclosure will be further clarified by a consideration of the following examples, which are intended to be purely exemplary of the use of the invention. Other embodiments of the disclosure will be apparent to those skilled in the art from a consideration of this specification or practice of the process as disclosed herein.

In the examples that follow, reaction rate is reported as moles of aldehyde produced per liter of reaction fluid volume per hour (gmole/l/hr). The purities of propylene and syngas feeds (1:1 molar $CO:H_2$ unless otherwise stated) are greater than 99.8 percent.

General Procedure for Hydroformylation Process

Two stock solutions are prepared in dry, degassed toluene: one containing a rhodium catalyst precursor (dicarbonylacetylacetonato rhodium (I)) and a doubly open-ended bis-phosphite Ligand A, as shown hereinabove, and another containing triphenylphosphine. The solutions are transferred via vacuum into a 100 ml Parr mini-reactor. The resulting catalyst solution is then pre-heated under syngas for 20-30 minutes. Liquid propylene is charged to a feed system that is closable with valves at either end above the reactor, and precise amounts of propylene are pressured in to the reactor with syngas. Previously generated data regarding olefin/toluene vapor pressure at various temperatures is used to determine the actual syngas pressure. The propylene is introduced into the reactor and the reactor is brought to the desired pressure, which is maintained during the reaction by feeding more syngas as needed. Liquid reaction samples are taken periodically and analyzed on an Agilent Technologies 6890 Gas Chromatograph, equipped with a DB-1 30 m×0.32 mm, 1 um film column Component analysis is based on GC area percent exclusive of solvent.

COMPARATIVE EXPERIMENT 1

Using the General Procedure for Hydroformylation Process described hereinabove, the hydroformylation reactor is loaded with a catalyst comprising rhodium (75 ppm, as rhodium dicarbonyl acetylacetonate) and doubly open-ended bisphosphite Ligand A (4 equivalent/Rh) in toluene (20 ml). After pre-heating the catalyst solution to 80° C. under 1:1 syngas, propylene (4.7 g) is pressurized into the reactor with 1:1 syngas sufficient to give a total reaction pressure of 300 psig (167 psig syngas pressure). The reaction solution is analyzed at 30 and 60 minutes as described above. The results are shown in Table 1.

EXAMPLE 2

The procedure of Comparative Experiment 1 is repeated, with the exception of the addition of triphenylphosphine (4 equivalents/Rh). The results are shown in Table 1.

EXAMPLE 3

A procedure identical to that described in Example 2 is conducted, except that the reaction temperature employed is 90° C. The results are shown in Table 1.

TABLE 1

| | Temp (° C.) | Total syngas uptake (cc) | Conversion % | Max rate (g mol/l-hr) | Final N:I |
|---|---|---|---|---|---|
| Comparative Ex. 1 | 80 | 2404 | 75.8 | 1.8 | 45.0 |
| Example 2 | 80 | 2243 | 75.0 | 2.0 | 49.0 |
| Example 3 | 90 | 3351 | 84.9 | 3.1 | 53.0 |

The n:i ratio refers to the relative amounts of normal butyraldehyde product (n) to isobutyraldehyde product (i) in the mixture of aldehyde products. From Table 1 it is seen that the addition of triphenylphosphine did not adversely impact the reaction rate or product regioselectivity (N:I ratio) to the linear aldehyde.

COMPARATIVE EXPERIMENTS 4-5 AND EXAMPLES 6-7

Stability data are obtained in a small-scale continuous reaction system. Catalyst solutions consisting of 75 ppm Rh (as rhodium dicarbonyl acetylacetonate), and 4 equivalents of Ligand A per Rh in 25 ml tetraglyme are charged to each of four heavy-walled glass tubes, and remain there throughout the run. Two of the tubes are additionally charged with 4 equivalents of triphenylphosphine per Rh dissolved in 1 ml of toluene. Carbon monoxide, hydrogen, nitrogen and 1-butene are continuously fed into the 90° C. reactors. Volatiles, including the toluene and products are continually stripped out of the reactors with excess feed gases, and are analyzed via an in-line gas chromatograph. Reactor liquid levels are manually controlled by carefully balancing the reaction and feed rates. Total gas flow through the reactors is 15-20 standard liters/hr. Conversion rates are 20-30%, total pressure is maintained at 150 psig.

Data for reactions with Rh/doubly open-ended bisphosphite Ligand A (Comparative Experiments 4 and 5) and Rh/doubly open-ended bisphosphite Ligand A/triphenylphosphine (examples 6 and 7) appear in Table 2.

TABLE 2

| Day | Comp. Ex. 4 (N:I) | Com. Ex. 5 (N:I) | Example 6 (N:I) | Example 7 (N:I) |
|---|---|---|---|---|
| 1 | 88 | 102 | NA | NA |
| 2 | 92 | 106 | 74 | 80 |
| 3 | 97 | 95 | 75 | 77 |
| 4 | 96 | 108 | 74 | 78 |
| 5 | 98 | 102 | 74 | 83 |
| 8 | 97 | 95 | 83 | 81 |
| 9 | 89 | 96 | 81 | 89 |
| 10 | 94 | 98 | 77 | 84 |
| 11 | 83 | 38 | 82 | 85 |
| 12 | 40 | 33 | 83 | 85 |
| 15 | 27 | 24 | 85 | 96 |
| 16 | 25 | 22 | 94 | 95 |
| 17 | 23 | 20 | 78 | 90 |
| 18 | 22 | 19 | 81 | 97 |
| 19 | 20 | 18 | 82 | 86 |
| 22 | 17 | 14 | 79 | 92 |

Product selectivity is an indicator of the nature of the catalyst complex, and the change of selectivity over time is an indicator of ligand stability. Comparative Experiments 4 and 5 without triphenylphosphine present clearly show signs of degradation after 11-12 days, while Examples 6 and 7 show no signs of degradation after 22 days.

The invention claimed is:

1. A hydroformylation process for continuous production of at least one aldehyde product, the process comprising the steps of: contacting under continuous reaction conditions in a hydroformylation reaction fluid, one or more olefinically-unsaturated compounds, carbon monoxide, and hydrogen in the presence of a mixture of a doubly open-ended organopolyphosphite ligand and an organomonophosphine ligand, at least one of said ligands being bonded to a transition metal to form a transition metal-ligand complex hydroformylation catalyst; the organopolyphosphite ligand comprising a plurality of phosphorus (III) atoms each bonded to three hydrocarbyloxy radicals, any non-bridging species of which consists essentially of an aryloxy radical (substituted or unsubstituted); the contacting being conducted in a manner such that the molar ratio of both the organomonophosphine and the organopolyphosphite to the metal is at least 1, and wherein the organomonophosphine ligand is triphenylphosphine and the organopolyphosphite ligand is of the formula:

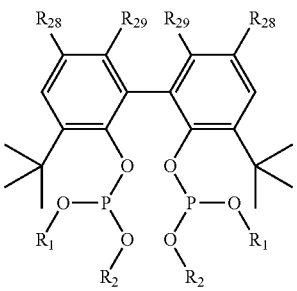

wherein each of $R_1$ and $R_2$ is the same or different and represents a substituted or unsubstituted monovalent aryl radical containing from 6 to 40 carbon atoms, and $R_{28}$ may be a $C_{1-20}$ alkyl or cycloalkly radical or an alkoxy radical; and $R_{29}$ may be a hydrogen atom, a $C_{1-20}$ alkyl or cycloalkyl radical or an alkoxy radical.

2. The process of claim 1 wherein the molar ratio of organopolyphosphite ligand to transition metal is increased or maintained by adding organopolyphosphite ligand to the reaction fluid.

3. The process of claim 1 wherein concentration of the transition metal is greater than about 1 part per million (ppm) and less than about 500 ppm, based on the weight of the hydroformylation reaction fluid.

4. The process of claim 1 wherein the process temperature is greater than about −25° C. and less than about 200° C.

5. The process of claim 1 wherein the total gas pressure comprising carbon monoxide, hydrogen, and olefinic reactant(s) is greater than about 25 psia (172 kPa) and less than about 2,000 psia (13,790 kPa).

6. The process of claim 1 wherein the olefin is an achiral alpha-olefin having from 2 to 30 carbon atoms or an achiral internal olefin having from 4 to 20 carbon atoms.

7. The process of claim 1 wherein carbon monoxide and hydrogen are present in quantities that provide an $H_2$:CO molar ratio ranging from 1:10 to 100:1.

8. The process of claim 1 wherein the transition metal is a Group VIII metal selected from rhodium, cobalt, iridium, ruthenium, and mixtures thereof.

9. The process of claim 1 wherein a mixture of organopolyphosphite ligands is employed.

10. A hydroformylation process comprising reacting one or more reactants, carbon monoxide, and hydrogen in the presence of a hydroformylation catalyst to produce a reaction product fluid comprising one or more products, wherein the reacting is conducted in the presence of a catalytic metal, a triarylphosphine compound, and a doubly open-ended bisphosphite ligand (Ligand A) of the formula:

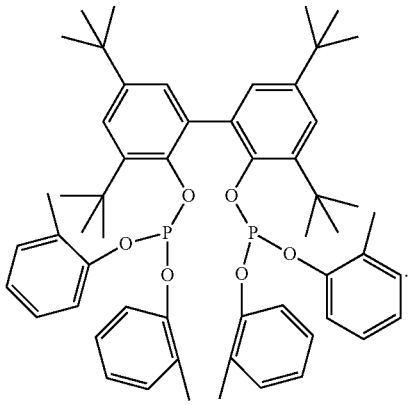 [SMILES: Cc1ccccc1OP(Oc1ccccc1C)Oc1c(-c2cc(C(C)(C)C)cc(C(C)(C)C)c2OP(Oc2ccccc2C)Oc2ccccc2C)cc(C(C)(C)C)cc1C(C)(C)C]

11. A hydroformylation process for continuous production of at least one aldehyde product, the process comprising the steps of: contacting under continuous reaction conditions in a hydroformylation reaction fluid, one or more $C_{2-4}$ achiral olefins, carbon monoxide, and hydrogen in the presence of a mixture of Ligand A of the formula:

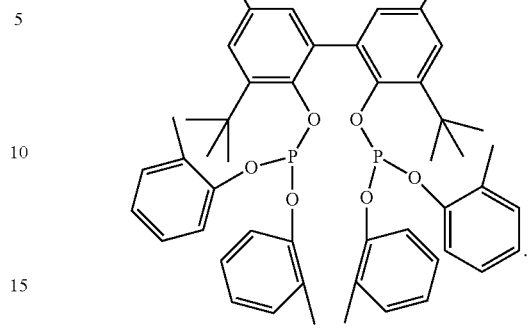

and triphenylphosphine, at least one of said ligands being bonded to a transition metal to form a transition metal-ligand complex hydroformylation catalyst wherein the metal comprises rhodium, the contacting being conducted in a manner such that the molar ratio of both the organomonophosphine and the organopolyphosphite to the metal is at least 1, the process temperature is greater than about −25° C. and less than about 200° C., and the total gas pressure comprising carbon monoxide, hydrogen, and olefinic reactant(s) is greater than about 25 psia (172 kPa) and less than about 2,000 psia (13,790 kPa).

* * * * *